United States Patent
Stock

(10) Patent No.: US 7,541,192 B2
(45) Date of Patent: Jun. 2, 2009

(54) PROCESS FOR DISTINGUISHING WET FROM DRY GAS WITH A BREATH ALCOHOL MEASURING DEVICE

(75) Inventor: Burkhard Stock, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 811 days.

(21) Appl. No.: 11/183,124

(22) Filed: Jul. 14, 2005

(65) Prior Publication Data

US 2006/0078467 A1    Apr. 13, 2006

(30) Foreign Application Priority Data

Oct. 8, 2004   (DE) .................. 10 2004 049 064

(51) Int. Cl.
*G01N 31/00* (2006.01)
(52) U.S. Cl. .................. 436/132; 73/23.3; 204/431; 204/432; 422/84
(58) Field of Classification Search .................. 422/84; 436/132; 73/23.3; 204/431, 432
See application file for complete search history.

(56) References Cited

FOREIGN PATENT DOCUMENTS

| DE | 43 27 312 C2 | 2/1994 |
|---|---|---|
| EP | 1 371 982 A1 | 12/2003 |

*Primary Examiner*—Jill Warden
*Assistant Examiner*—Dwan A Gerido
(74) *Attorney, Agent, or Firm*—McGlew and Tuttle, P.C.

(57) ABSTRACT

A process is provided for distinguishing between wet from dry gas with a breath alcohol measuring device, in which a defined sample volume from a gas blown in is fed for sampling to an electrochemical sensor (6), which generates a sensor signal that depends on the reaction of ethyl alcohol. The sensor signal is sent to a control and evaluating unit (4) and is evaluated there to determine the alcohol concentration. To distinguish dry gas from wet gas, provisions are made for the sensor signal to be detected in its time dependence and for the presence of wet gas to be determined when it is observed that a sensor signal of a polarity opposite the polarity of the sensor signal caused by the reaction of ethyl alcohol appeared at first at the beginning of sampling. The process may be used, e.g., in conjunction with the calibration of breath alcohol measuring devices or in so-called interlock systems with a breath alcohol measuring device in order to recognize attempts at manipulation.

11 Claims, 2 Drawing Sheets

PROCESS FOR DISTINGUISHING WET FROM DRY GAS WITH A BREATH ALCOHOL MEASURING DEVICE

CROSS REFERENCE TO RELATED APPLICATIONS

This application claims the benefit of priority under 35 U.S.C. § 119 of German Application DE 10 004 049 064.3 filed Oct. 8, 2004, the entire contents of which are incorporated herein by reference.

FIELD OF THE INVENTION

The present invention pertains to a process for distinguishing wet from dry gas with a breath alcohol measuring device, in which a defined sample volume from a gas blown in is fed to an electrochemical sensor, which generates a sensor signal that depends on the reaction of ethyl alcohol, sends the sensor signal to a control and evaluating unit, and the sensor signal is evaluated there to determine an alcohol concentration.

BACKGROUND OF THE INVENTION

Breath alcohol measuring devices are known, for example, from DE 43 27 312 C2 and EP 1 371 982 A1. The test subject blows breathing air via a mouthpiece into such breath alcohol measuring devices, and the breathing air is then sent through a measuring channel, in which a signal representative of the tidal volume flow is generated, usually by a pressure sensor, and the signal is sent to a control and evaluating unit. This tidal volume flow signal is needed, on the one hand, to make it possible to monitor the interruption-free breathing of the test subject. Furthermore, the tidal volume flow signal is integrated so that a preset minimum volume can be determined, which is needed for a reliable measurement result, because a sufficient percentage of the breathing air needs to originate from the depth of the lungs in order to make it possible to infer the blood alcohol concentration from the breath alcohol concentration.

A defined sample volume is drawn off from the measuring channel by means of a pumping means and fed to an electrochemical sensor. Ethyl alcohol is reacted at the electrodes of the electrochemical sensor, and an electric current is generated, which slowly subsides after a rapid rise, which corresponds to the subsiding reaction. The sensor current is integrated for a preset period of time in the control and evaluating unit, and the overall charge is estimated from this integrated charge value, from which the breath alcohol concentration can be derived.

Two methods are available, in principle, for the calibration of breath alcohol measuring devices. On the one hand, a test gas of a known composition is blown from a pressure cylinder into the breath alcohol measuring device or, on the other hand, an air flow, which is passed through an alcohol-water mixture of constant temperature (usually 34° C.), is blown into the breath alcohol measuring device. One speaks of using wet gas in the case of the latter method, because the air is enriched not only with alcohol, but also with water vapor. Both procedures have specific advantages and disadvantages in practice. Test gas in pressure cylinders can be transported more easily and requires no devices for heating and temperature control. The drawback of the use of test gas is the dependence of the result on the barometric pressure. A corresponding correction of the results and consequently of the calibration is necessary in case of deviations from the normal pressure. On the other hand, even though wet gas is substantially independent from the outside pressure and more similar to the breathing air, it does require a heating means and a heated gas carrying system to avoid condensation, so that dry gas is used increasingly frequently in practice.

A problem arises in connection with the use of the two procedures described due to the difference in the sensitivity of the electrochemical sensor to dry gas, on the one hand, and wet gas, on the other hand: At equal alcohol concentration, dry gas leads to a measured value that is lower by about 10% than wet gas. Half of the effect can be explained by the absorption of the water in the sample on the sensor surface, but the cause of the other half of the effect is still unknown.

The breath alcohol measuring device must therefore be informed in practice by an input of the type of gas used for the calibration or the routine testing. The device must have special input means for this purpose. Considerable errors in measurement and consequently considerable calibration errors may result from mistakes or from the incorrect entry of the test gas.

The test subject, i.e., the user, must blow into a breath alcohol measuring device in case of the use of breath alcohol measuring devices in so-called interlock systems, after which a means arranged downstream, e.g., access to a machine or the starter of a motor-driven vehicle, is either released or blocked depending on the measured breath alcohol level. The recognition of attempts at manipulation, e.g., blowing through an activated carbon filter, is of great significance in such interlock systems. Such attempts at manipulation have hitherto been recognized by additional technical measures, e.g., the measurement of the breath temperature or the measurement of the moisture content in the breathing air blown in with a moisture sensor. However, this is associated with increased technical effort.

SUMMARY OF THE INVENTION

The object of the present invention is to provide a process for distinguishing wet from dry gas blown in, which can be carried out automatically with a breath alcohol measuring device.

According to the invention a process for distinguishing wet from dry gas with a breath alcohol measuring device is provided in which a defined sample volume from a gas blown in is fed for sampling to an electrochemical sensor. The sensor generates a sensor signal, which depends on the reaction of ethyl alcohol. The sensor signal is sent to a control and evaluating unit and is evaluated there to determine an alcohol concentration. The sensor signal is detected as a function of time. The presence of wet gas is determined when it is determined in a control and evaluating unit that a sensor signal with a polarity opposite the polarity of the sensor signal caused by the reaction of ethyl alcohol has appeared at first at the beginning of sampling.

Provisions are made for the sensor signal to be detected as a function of the time and analyzed by the control and evaluating unit. If it is determined in the process that a sensor signal of a polarity that is opposite the polarity of the sensor signal that is caused by the reaction of ethyl alcohol appeared at first, the presence of wet gas is determined, because it was found that during the initial phase, wet gas first causes a short sensor signal whose polarity is opposite the polarity of the ethyl alcohol signal.

The electrochemical sensor usually delivers a positive signal due to the reaction of ethyl alcohol. The sensor signal rises rapidly (in about 2 sec) to a maximum after the admission of the gas from the sample volume to drop subsequently exponentially to the initial value. The concentration is calculated from the area under the curve. This applies to both dry gas and wet gas. The difference between dry gas and wet gas is seen immediately after the beginning of sampling. In case of dry gas, the sensor signal already rises steeply with the beginning of the sampling. The ethyl alcohol molecules are consequently reacted immediately in the electrochemical sensor. However, the response behavior is different in case of wet gas. A negative signal is observed at first immediately after the beginning of the sampling. The rise of the sensor signal because of the electrochemical reaction of the ethyl alcohol takes place only thereafter. Consequently, the reaction of ethyl alcohol takes place with a delay compared to that seen in dry gas. By detecting this short signal, which initially has an opposite polarity, it is consequently possible to infer the presence of dry gas. The sample volume should be fed to the electrochemical sensor so quickly that the sensor signal of opposite polarity can be readily detected in case of wet gas. The sampling should take place in less than 50 msec and preferably between 15 msec and 40 msec in practically relevant applications.

The presence of the initial sensor signal of opposite polarity can be determined, e.g., from the fact that the difference is formed from the sensor signal that is present when a first extreme value is reached in the time curve of the sensor signal and the signal before the beginning of sampling and a check is performed to determine whether the difference has the expected opposite polarity and a value that is greater than a first preset threshold value. As an alternative or in addition, the presence of a sensor signal with an initially opposite polarity can be detected on the basis of the time delay of the sensor signal when the sensor signal is still below a preset second threshold value after a preset time after the beginning of sampling.

To achieve a sufficient time resolution of the sensor signal, the time dependence of the sensor signal is scanned at a frequency of at least 100 Hz, i.e., at least 100 measured values of the sensor signal are recorded per second.

The process according to the present invention can also be used in a method for calibrating the breath alcohol measuring device, so that it is automatically determined whether dry gas or wet gas is used as the test gas, and the calibration can be correspondingly adapted.

The process according to the present invention can be used, furthermore, in a process for detecting attempts at manipulation on a breath alcohol measuring device, which is used to release a connected device, by the connected device being released or blocked only when the measured breath alcohol concentration is below a preset limit value and the presence of wet gas is determined by detecting a sensor signal of an initially opposite polarity.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
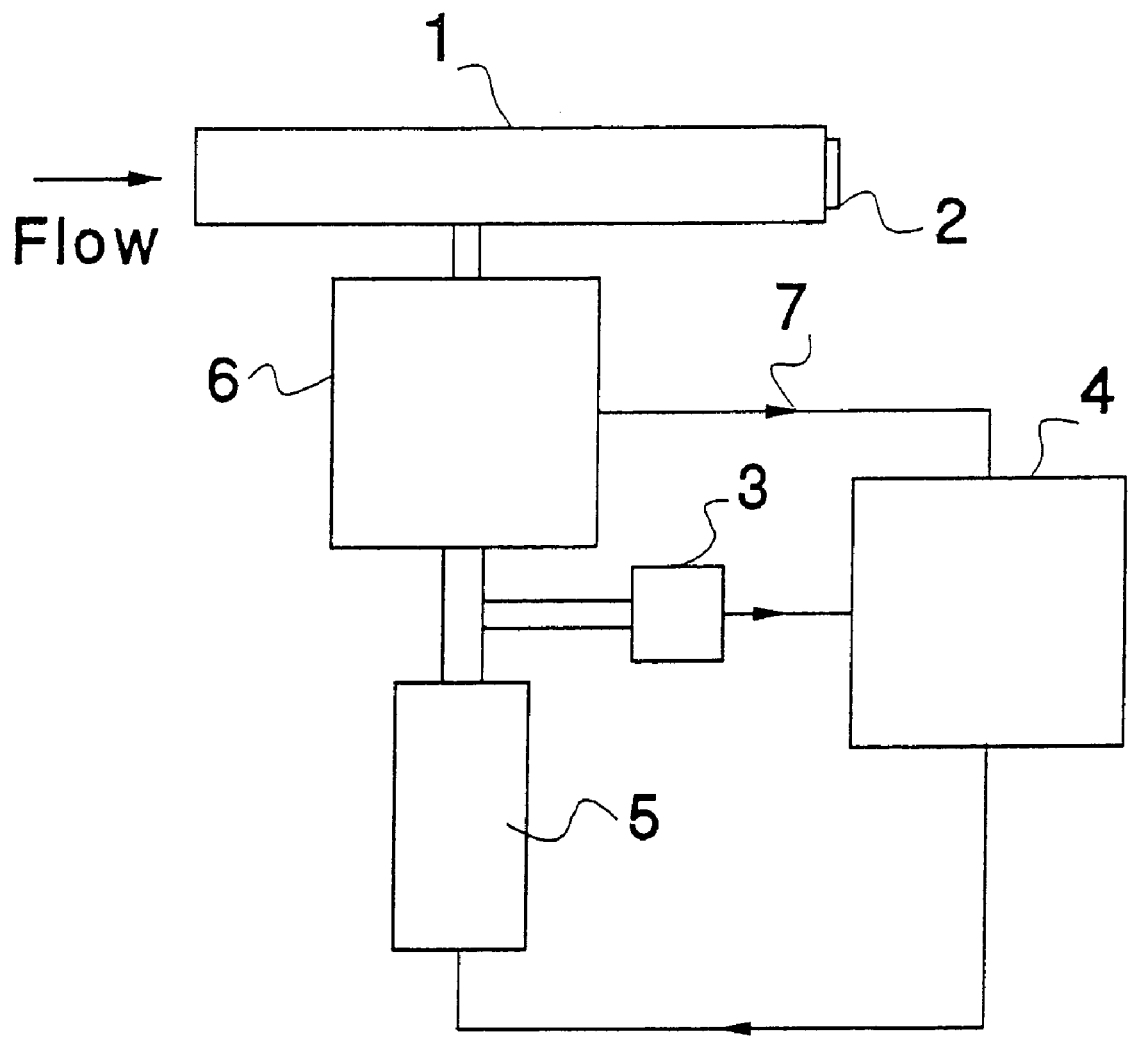
FIG. 1 is a schematic view showing the design of a breath alcohol measuring device for carrying out the present invention.

Referring to the drawings in particular, FIG. 1 schematically shows the design of a breath alcohol measuring device. The test subject blows into a replaceable mouthpiece 1. The dynamic pressure generated by the breath flow in a diaphragm 2 is measured with the pressure sensor 3, and a breath flow (volume flow) is calculated from the pressure sensor signal in the control and evaluating unit 4. When the test subject has released a predetermined, sufficient amount of air, a defined sample volume is drawn off from the breathing air into the electrochemical sensor 6 with the pump 5. The sampling operation is preferably carried out very rapidly, preferably in less than 50 msec, e.g., in 30 msec. Such a short sampling phase is preferred in order to reach a sufficient sensitivity to the different response behaviors of the electrochemical sensor to dry gas and wet gas.

The alcohol molecules in the sample volume are absorbed on the surface of the electrochemical sensor 6 and electrochemically reacted. The sensor signal generated hereby is sent via the connections 7 to the control and evaluating unit 4. The sensor signal is scanned at a high frequency in order to reach a sufficient time resolution for the time curve of the sensor signal. At least 100 measurements should be recorded per second.

Figure 2:
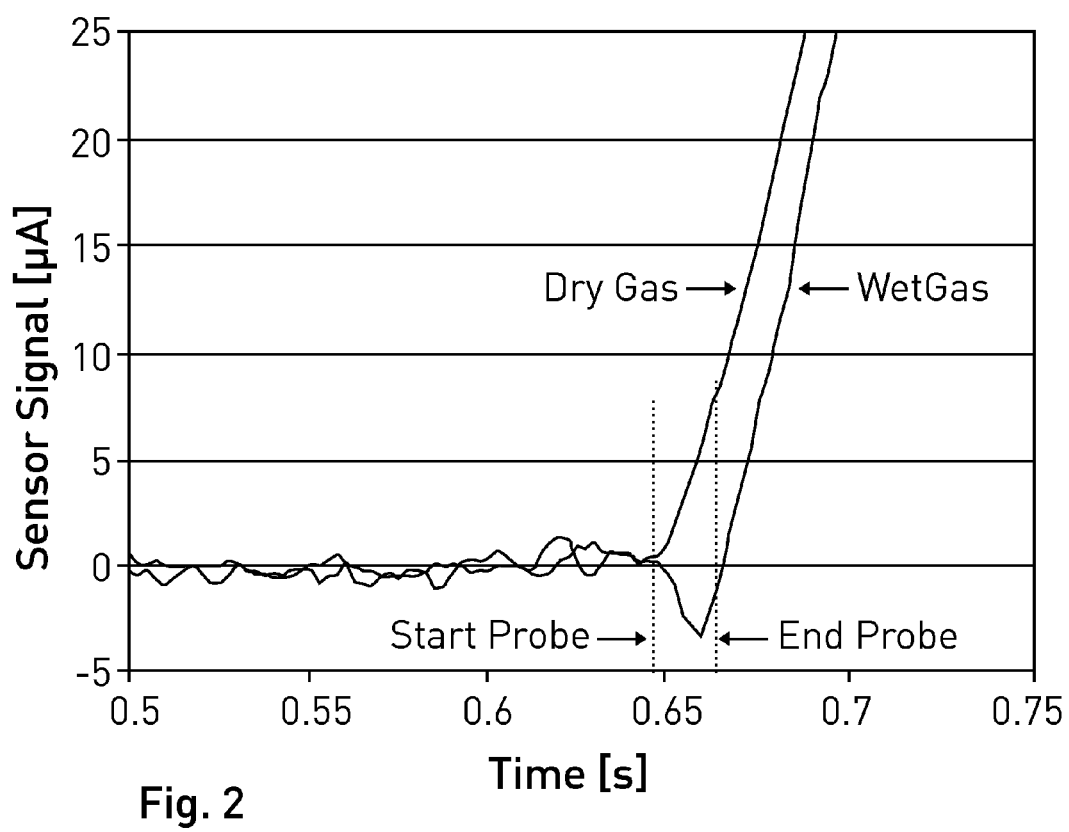
FIG. 2 is a diagram showing the time dependence of the sensor signal upon the admission of dry gas and wet gas for comparison into the electrochemical sensor.

The time curves of the sensor signals for dry gas and wet gas are compared in FIG. 2. The signals rise rapidly to a maximum (in about 2 sec) upon the admission of gas and subsequently drop exponentially to the initial value (only the initial phase of the rapid rise is shown in FIG. 2). The alcohol concentration is calculated from the area under the curve. This applies to both dry gas and wet gas. The difference between dry gas and wet gas is seen immediately after the beginning of the sampling, the beginning and the end of the pumping operation during sampling being indicated by broken lines in FIG. 2.

In case of dry gas, the sensor signal already rises rapidly immediately with the beginning of sampling. The alcohol molecules are consequently reacted immediately in the sensor.

However, a different response behavior is seen in the case of wet gas. A negative signal curve (opposite the polarity of the ethyl alcohol signal), whose duration approximately corresponds to that of the sampling, is seen at first immediately after the beginning of the sampling. The signal rises only thereafter because of the electrochemical reaction of the ethyl alcohol in the electrochemical sensor 6. Consequently, the reaction of the ethyl alcohol is delayed compared to that in dry gas.

The measurement of the delay and/or the detection of the initially opposite, here negative, signal make it therefore possible to set threshold values for a distinction between dry gas and wet gas. The value of the sensor signal, and consequently also the threshold values, depend on the sample volume that is drawn into the sensor. The sample volume was approx. 0.5 $cm^3$, a typical value for practice, for the signals in FIG. 2.

For example, the difference between the sensor current at the minimum after the beginning of sampling and the signal obtained immediately before the beginning of sampling is formed as the parameter for the evaluation of the sensor signal of opposite polarity. To infer a negative signal, this difference must be negative, and it should exceed a certain value in order to be set off from the sensor noise. For example, a sensor current difference of −2 µA can be selected as the threshold value. The difference of the sensor current values at the minimum after the beginning of sampling and the sensor current immediately before the beginning of sampling is −3.5 μA for wet gas in the example shown in FIG. 2, whereas no value lower than 0 can be found at all in case of dry gas.

For example, the value of the sensor signal at the end of the pumping operation for sampling may be used to determine another parameter; this parameter is representative of the delay of the sensor signal. The threshold for the distinction between dry gas and wet gas shall be, e.g., 4 μA in the case of the breath alcohol measuring device being used here and an alcohol concentration of 250 ppm. This parameter is −3.5 μA for wet gas and +8 μA for dry gas in the example shown in FIG. 2.

Wet and dry gas can be unambiguously distinguished with these two parameters, which can be evaluated both individually and in their combination.

The control and evaluating unit 4 is prepared in terms of programming such that the time curve can be recorded and the sensor signal can be evaluated automatically in the manner described. It is obvious that the electronic circuits for signal processing and analog/digital reaction are designed such that they cause the least possible distortion in the time curve of the sensor signal and offer a sufficient time resolution.

The process described can be used in connection with a calibration operation, in which a test gas is blown into the breath alcohol measuring device. The breath alcohol measuring device can automatically determine whether the gas is a dry gas or a wet gas and take this into account in the calibration.

Besides, the process may also be used in connection with so-called interlock systems. These are processes in which a breath alcohol measuring device is used to grant access for a user to a machine or a vehicle or the like depending on the measured value sent by the breath alcohol measuring device. Attempts at manipulation, e.g., attempts at removing the alcohol from the breathing air by means of activated carbon filters or the like, should be recognized in this case to the greatest extent possible, because such filters also always act as potent desiccants. Consequently, the total amount of moisture is also extensively removed from the breathing air, besides the alcohol. Using the process according to the present invention, it is now possible to determine that the test subject's breathing air is not wet gas, but dry gas, which unambiguously indicates an attempt at manipulation, and release of the machine, vehicle or the like can then be blocked.

While specific embodiments of the invention have been shown and described in detail to illustrate the application of the principles of the invention, it will be understood that the invention may be embodied otherwise without departing from such principles.

What is claimed is:

1. A process for distinguishing wet from dry gas with a breath alcohol measuring device, the process comprising the steps of:

feeding a defined sample volume from a gas blown in the breath alcohol measuring device for sampling to an electrochemical sensor; determining the polarity of the sensor signal at the beginning of sampling using the electrochemical sensor to generate a sensor signal based on the step of feeding, with the sensor signal depending on the reaction of ethyl alcohol;

sending the sensor signal to a control and evaluating unit;

evaluating the sensor signal at the control and evaluating unit to determine an alcohol concentration including detecting the sensor signal as a function of time and determining the polarity of the sensor signal caused by reaction of alcohol and then determining the presence of wet gas when it is determined in the control and evaluating unit that a sensor signal with a polarity opposite the polarity of the sensor signal caused by the reaction of ethyl alcohol has appeared at first at the beginning of the sampling.

2. A process in accordance with claim 1, wherein determining a sensor signal of opposite polarity includes:

obtaining a sensor signal after sampling has started;

obtaining a sensor signal before the beginning of sampling;

determining a difference of the sensor signal after sampling has started and the sensor signal before the beginning of sampling; and determining if the difference is of a negative polarity and a value that is greater than a first preset threshold value.

3. A process in accordance with claim 1, wherein determining the sensor signal of opposite polarity includes:

obtaining the sensor signal after a predetermined time after the beginning of the sampling; and determining if the obtained sensor signal is below a preset threshold value after the predetermined time after the beginning of the sampling.

4. A process in accordance with claim 3, wherein the predetermined time is defined by the duration of sampling.

5. A process in accordance with claim 2, wherein determining the sensor signal of opposite polarity further includes:

obtaining a sensor signal after a predetermined time after the beginning of the sampling; and determining if the obtained sensor signal is below a preset second threshold value after the predetermined time after the beginning of the sampling.

6. A process in accordance with claim 5, wherein the presence of the sensor signal of opposite polarity is determined only when the condition of the first threshold value and that of the second threshold valve are met in a combined manner.

7. A process in accordance with claim 1, wherein the duration of sampling is shorter than 50 msec.

8. A process in accordance with claim 7, wherein the duration of sampling is between 15 msec and 40 msec.

9. A process in accordance with claim 1, wherein at least 100 measured values of the sensor signal are recorded per second to detect the time dependence of the sensor signal.

10. A process according to claim 1, wherein said step of feeding a defined sample volume from a gas blown in the breath alcohol measuring device for sampling to the electrochemical sensor includes feeding a test gas into the breath alcohol measuring device; and said step of evaluating the sensor signal provides an indication of whether wet gas or dry gas is being used as the test gas, and this is taken into account for calibrating the breath alcohol measuring device.

11. A process according to claim 1, wherein said step of evaluating the sensor signal provides an indication of whether wet gas or dry gas is being fed and further comprising the step of:

determining that an attempt at manipulation has occurred when dry gas is detected.

* * * * *